(12) United States Patent
Okumura et al.

(10) Patent No.: US 11,123,037 B2
(45) Date of Patent: Sep. 21, 2021

(54) X-RAY IMAGING APPARATUS

(71) Applicant: Shimadzu Corporation, Kyoto (JP)

(72) Inventors: Hiroshi Okumura, Kyoto (JP); Ken Shirota, Kyoto (JP); Junpei Sakaguchi, Kyoto (JP); Toshiya Kawabata, Kyoto (JP)

(73) Assignee: Shimadzu Corporation, Kyoto (KR)

( * ) Notice: Subject to any disclaimer, the term of this patent is extended or adjusted under 35 U.S.C. 154(b) by 73 days.

(21) Appl. No.: 16/823,016

(22) Filed: Mar. 18, 2020

(65) Prior Publication Data

US 2020/0367848 A1  Nov. 26, 2020

(30) Foreign Application Priority Data

May 21, 2019 (JP) .............................. JP2019-095306

(51) Int. Cl.
*A61B 6/00* (2006.01)
*A61B 90/00* (2016.01)

(52) U.S. Cl.
CPC ............... *A61B 6/54* (2013.01); *A61B 6/40* (2013.01); *A61B 6/42* (2013.01); *A61B 6/4452* (2013.01); *A61B 6/4464* (2013.01); *A61B 6/467* (2013.01); *A61B 90/361* (2016.02)

(58) Field of Classification Search
CPC .................................. A61B 6/107; A61B 6/10
See application file for complete search history.

(56) References Cited

U.S. PATENT DOCUMENTS

2020/0187877 A1* 6/2020 Chakrabarti ........... A61B 6/542

FOREIGN PATENT DOCUMENTS

JP        2012-239534 A      12/2012

* cited by examiner

*Primary Examiner* — Dani Fox
(74) *Attorney, Agent, or Firm* — Muir Patent Law, PLLC

(57) ABSTRACT

An X-ray imaging apparatus includes an X-ray source, a detector for detecting X-rays, an imaging unit, an operation unit, a notification unit, and a control unit. The control unit generates an image of an inside of an examination room. Further, when detecting that a person other than a subject is present in the examination room based on the image of the inside of the examination room, the control unit performs control to issue caution information indicating that a person other than a subject is present in the examination room.

13 Claims, 10 Drawing Sheets

(First modification)

(Second modification)

(Third modification)

X-RAY IMAGING APPARATUS

CROSS-REFERENCE TO RELATED APPLICATIONS

The priority application number No. JP2019-095306, entitled "X-ray imaging apparatus", filed on May 21, 2019, and invented by OKUMURA Hiroshi, SHIROTA Ken, SAKAGUCHI Junpei, and KAWABATA Toshiya, upon which this patent application is based, is hereby incorporated by reference.

BACKGROUND OF THE INVENTION

Field of the Invention

The present invention relates to an X-ray imaging apparatus.

Description of the Background Art

Conventionally, an X-ray imaging apparatus is known. Such an X-ray imaging apparatus is disclosed, for example, in Japanese Unexamined Patent Application Publication No. 2012-239534.

The Japanese Unexamined Patent Application Publication No. 2012-239534 discloses an X-ray imaging apparatus including a fluoroscopy table, an X-ray tube device, an X-ray detector, an X-ray high-voltage device, and an operator console. The fluoroscopy table, the X-ray tube device, the X-ray detector, and the X-ray high-voltage device are installed in an imaging room, and the console is installed in an operation room adjacent to the imaging room.

A window is provided between the imaging room and the operation room. An examiner performs an operation of irradiating X-rays with an operation console while monitoring the interior of the imaging room through the window.

However, even if a person other than a subject is present in an examination room, in some cases, it cannot be confirmed through the window. If an examiner operates to emit X-rays in a state in which a person other than a subject is present in the examination room, the person other than the subject may be unnecessarily exposed. Therefore, in order to prevent a person other than a subject from being unnecessarily exposed, it is conceivable that an examiner does not confirm through the windows, but rather confirms, for example, by entering into the examination room. However, in cases where the inside of the examination room is checked every time the examiner performs an operation of emitting X-rays, the burden on the examiner increases.

SUMMARY OF THE INVENTION

The present invention has been made to solve the above-mentioned problems, and an object of the present invention is to provide an X-ray imaging apparatus capable of suppressing a burden on an examiner from being increased and notifying that a person other than a subject is present in an examination room even when a person other than a subject is in a position where it is difficult to confirm through a window.

Means for Solving the Problems

In order to achieve the above-described object, an X-ray imaging apparatus according to one aspect of the present invention is provided with an X-ray source arranged in an examination room, a detector arranged in the examination room for detecting X-rays emitted from the X-ray source, an imaging unit configured to image a person who is present in the examination room, an operation unit arranged outside the examination room and configured to receive an operation input, a notification unit, and a control unit configured to generate an image of an inside of the examination room based on an imaging result captured by the imaging unit and configured to perform control to make the notification unit issue caution information indicating that a person other than a subject is present in the examination room when the person other than the subject is present in the examination room is detected based on the generated image of the inside of the examination room.

Effects of the Invention

The X-ray imaging apparatus according to one aspect of the present invention includes, as described above, an imaging unit configured to image a person in the examination room and a controller configured to perform control to generate an image in the examination room based on an imaging result imaged by the imaging unit and to perform control to make a notification unit issue caution information indicating that a person other than a subject is present in an examination room when it is detected that a person other than a subject is present in the examination room based on a generated image in the examination room. With this, it is possible to alert to the examiner who performs the operation to emit X-rays at the outside of the examination room that a person other than a subject is present in the examination room, without directly requiring direct checking of the inside of the examination room. As a result, it is possible to suppress the burden on the examiner from increasing, and it is also possible to notify that a person other than a subject is present in the examination room even when a person other than a subject is present in a position where it is difficult to confirm through the windows. In addition, for example, as compared with a configuration in which a person in an examination room is detected by a range finder such as an infra-red sensor or thermography, the positional relation of the person who is present in the examination room can be detected in detail. As a result, it is possible to improve the detection accuracy of the person who is present in the examination room.

DESCRIPTION OF PREFERRED EMBODIMENTS

Hereinafter, embodiments in which the present invention is embodied will be described with reference to the attached drawings.

Figure 1:
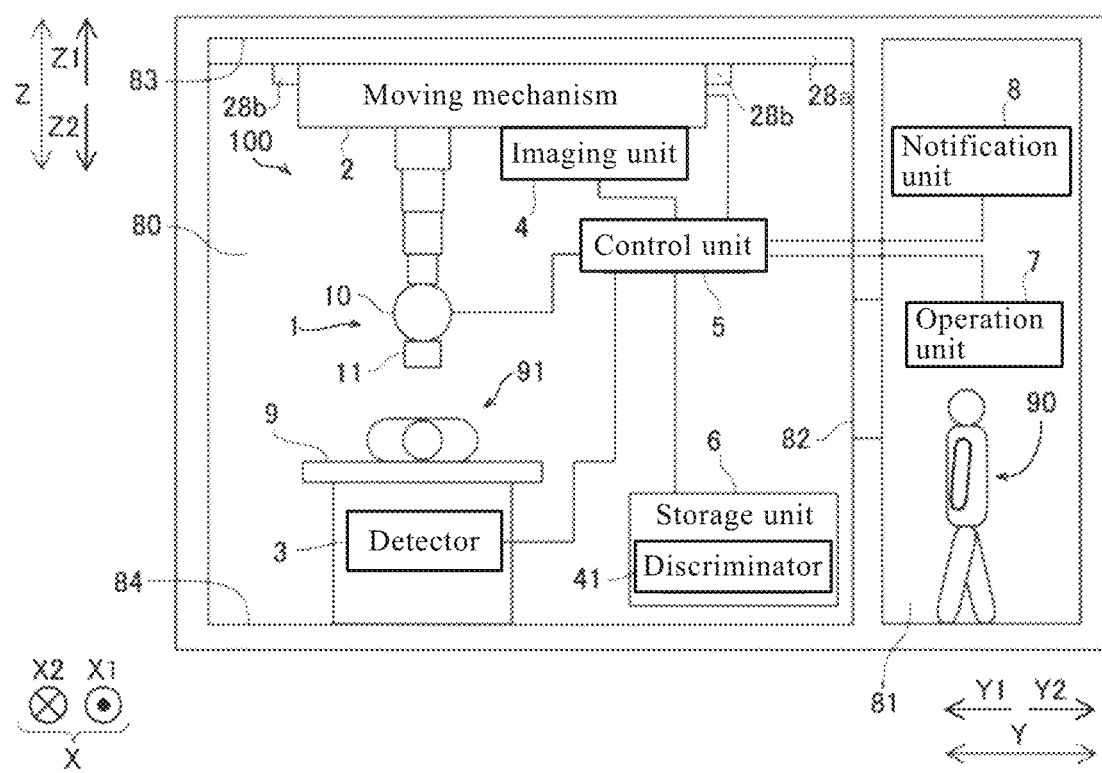
FIG. 1 is a block diagram showing an entire configuration of an X-ray imaging apparatus according to an embodiment.
Figure 2:
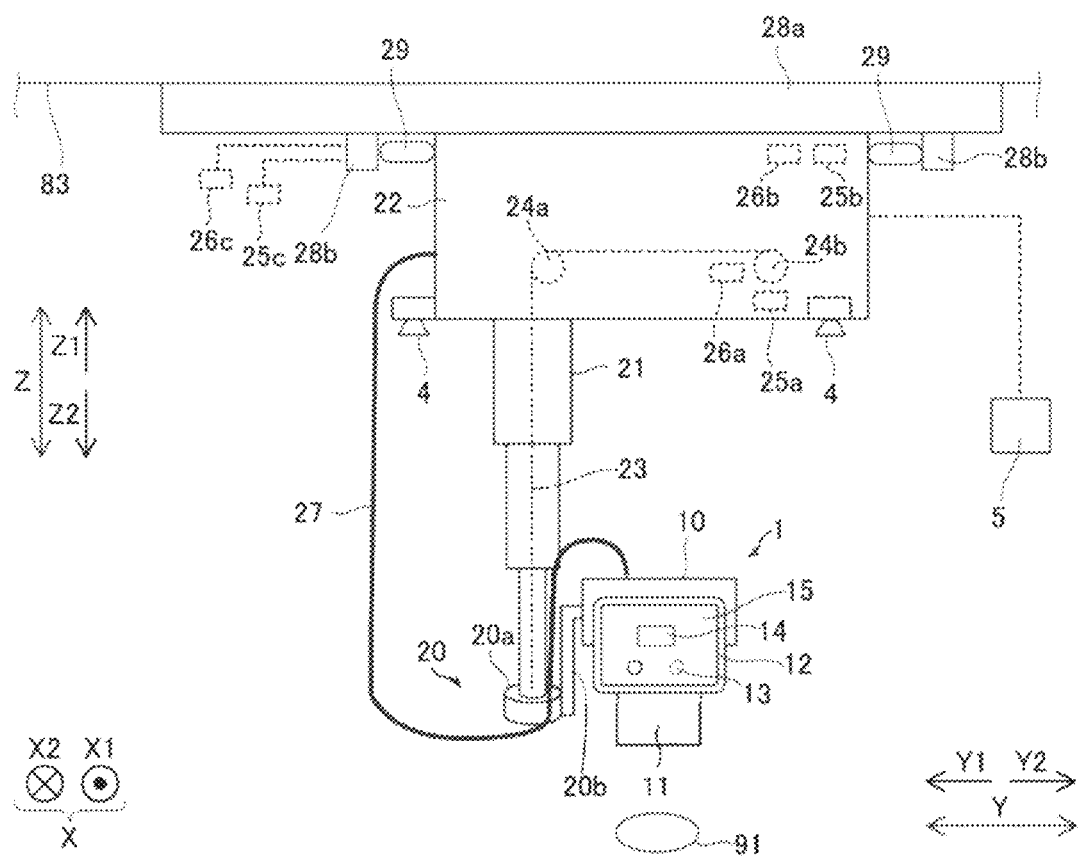
FIG. 2 is a schematic diagram showing a configuration of an X-ray imaging apparatus according to an embodiment.
Figure 3:
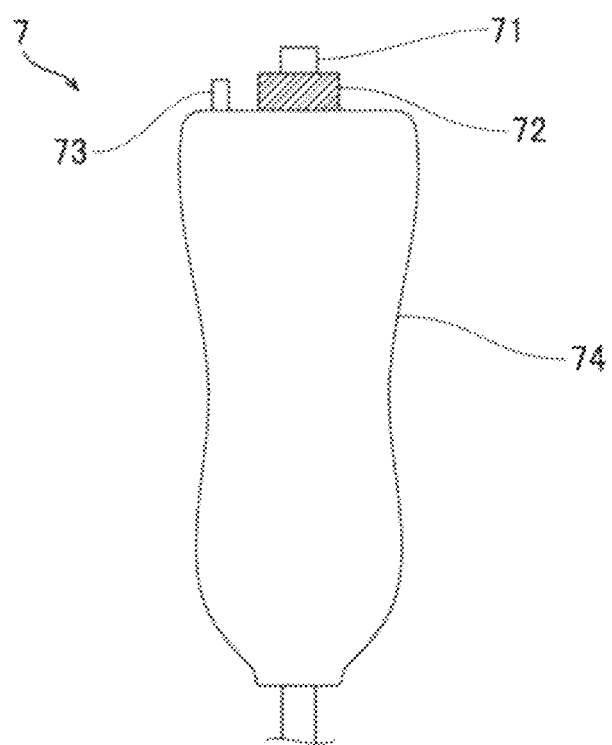
FIG. 3 is a schematic side view of an operation unit of an X-ray imaging apparatus according to an embodiment.
Figure 4:
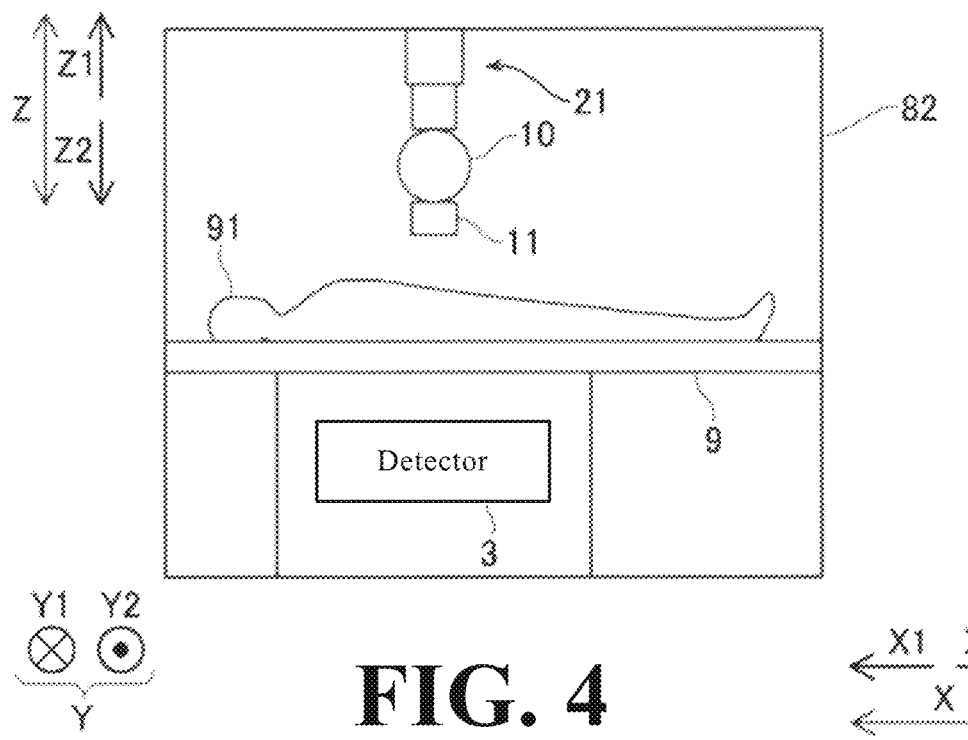
FIG. 4 is a schematic diagram for explaining a range in an examination room visible from a window.

With reference to FIG. 1 to FIG. 3, a configuration of an X-ray imaging apparatus 100 according to an embodiment will be described.

(Configuration of X-Ray Imaging Apparatus)

As shown in FIG. 1, the X-ray imaging apparatus 100 of this embodiment includes an X-ray generation unit 1, a moving mechanism 2, a detector 3, an imaging unit 4, a control unit 5, a storage unit 6, an operation unit 7, and a notification unit 8. The X-ray generation unit 1, the detector 3, the imaging unit 4, the control unit 5, and the storage unit 6 are provided in an examination room 80. The operation unit 7 and the notification unit 8 are arranged outside the examination room 80. Specifically, the operation unit 7 and the notification unit 8 are provided in an operation room 81 adjacent to the examination room 80. Note that the control unit 5 and the storage unit 6 may be provided in either the examination room 80 or the operation room 81.

A window 82 is provided between the examination room 80 and the operation room 81. In the operation room 81, an examiner 90 performs an operation of emitting X-rays by the operation unit 7 while checking the inside of the examination room 80 through the window 82.

The X-ray generation unit 1 includes an X-ray source 10. The X-ray source 10 is configured to emit X-rays when a high-voltage current is applied thereto. A collimator 11 is provided at a lower portion of the X-ray source 10. The collimator 11 is configured to narrow down the irradiation range of the X-rays emitted from the X-ray source 10. The collimator 11 is configured by combining flat plates such as, e.g., lead plates.

The moving mechanism 2 is configured to movably hold 41 the X-ray source 10. The moving mechanism 2 is provided on the ceiling 83 of the examination room 80. The detailed configuration of the moving mechanism 2 will be described later.

The detector 3 is configured to detect X-rays emitted from the X-ray source 10. In the embodiment shown in FIG. 1, the detector 3 is provided below the top board 9 on which a subject 91 is placed. The detector 3 includes, for example, an FPD (Flat Panel Detector).

The imaging unit 4 is configured to capture an image 50 of the inside of the examination room 80. The control unit 5 is configured to detect a person who is present in the examination room 80 by analyzing the image 50 in the examination room 80 captured by the imaging unit 4. In this embodiment, the imaging unit 4 is composed of a stereo camera. The stereo camera uses two cameras (two-eye cameras) to simultaneously image a person who is present in the examination room 80 from a plurality of different directions. With this, it is possible to three-dimensionally discriminate a person from the position information of pixels of the stereo camera. The imaging unit 4 is provided on the moving mechanism 2.

The control unit 5 is configured to perform control to make the notification unit 8 issue caution information 40 (see FIG. 9) indicating that a person 92 (see FIG. 5) other than a subject 91 is present in the examination room 80. The control unit 5 is composed of a computer including a processor, such as, e.g., a CPU (Central Processing Unit) and an FPGA (Field Programmable Gate Array), a GPU (Graphics Processing Unit), and a volatile and/or nonvolatile memory. The detail of the control that the control unit 5 notifies an examiner of the caution information 40 will be described later.

Figure 5:
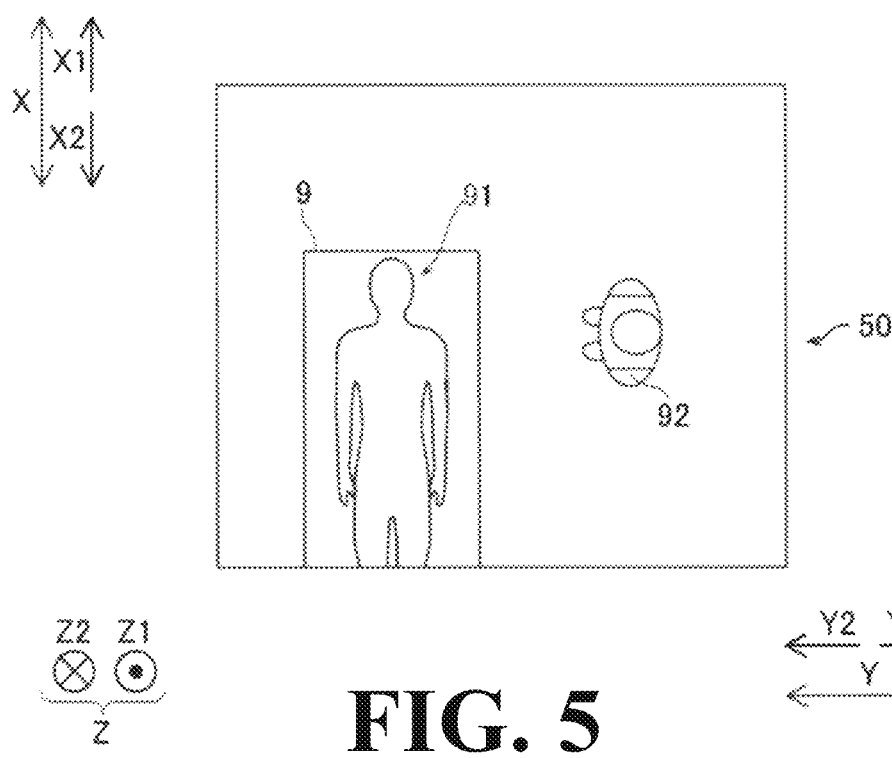
FIG. 5 is a schematic diagram showing an image detected by an imaging unit.

The storage unit 6 stores various programs executed by the control unit 5. The storage unit 6 also stores a discriminator 41 used when the control unit 5 determines whether or not a person 92 other than a subject 91 is present in the examination room 80, as shown in FIG. 5. The storage unit 6 includes, for example, an HDD (Hard Disk Drive) or a nonvolatile memory.

The operation unit 7 is configured to be able to accept an operation input by the examiner 90. The detailed configuration of the operation unit 7 will be described later.

The notification unit 8 is configured to issue caution information 40 (see FIG. 9) under the control of the control unit 5. The notification unit 8 is provided in the operation room 81. The notification unit 8 is provided in the vicinity of the window 82 in the examination room 80. The detailed configuration of the notification unit 8 will be described later.

(X-Ray Generation Unit)

As shown in FIG. 2, a handle 12 is attached to the X-ray generation unit 1. The handle 12 is configured to be gripped by an examiner 90. The X-ray generation unit 1 is provided with an operation panel 15 including operation switches 13 and a display unit 14. In accordance with the operation of the operation panel 15 by an examiner 90, the rotation movement of the X-ray generation unit 1 about an axis along the vertical direction, and the vertical movement of the X-ray generation unit 1, and the horizontal movement of the X-ray generation unit 1 are performed.

(Moving Mechanism)

As shown in FIG. 2, the moving mechanism 2 is provided with a holding unit 20, a column unit 21, and a carriage unit 22.

The holding unit 20 is configured to hold the X-ray generation unit 1. Further, the holding unit 20 is attached to the lower portion of the column unit 21. The holding unit 20 includes a disk-shaped mounting portion 20a attached to the lower portion of the column unit 21 and an arm portion 20b connecting the mounting portion 20a and the X-ray generation unit 1. The disk-shaped mounting portion 20a is configured to be rotatable about a vertical axis with respect to the column unit 21. The X-ray generation unit 1 is configured to be rotatable about a horizontal axis with respect to the arm portion 20b.

The column unit 21 is configured to move the holding unit 20 (X-ray generation unit 1) vertically. Specifically, the column unit 21 is configured to be vertically expandable and contractible. The expansion and contraction of the column unit 21 causes the holding unit 20 to move vertically together with the X-ray generation unit 1. A wire rope 23 is provided inside the column unit 21. One end of the wire rope 23 is connected to the lower portion of the column unit 21. The other end of the wire rope 23 is connected to the drum 24b via a pulley 24a provided inside the carriage unit 22. A motor 25a is connected to the drum 24b. The drum 24b is provided with a brake 26a. When the wire rope 23 is wound on or unwound from the drum 24b by the rotation of the motor 25a, the column unit 21 expands and contracts. The rate of expansion and contraction of the column unit 21 (the vertical motion of the holding unit 20) is controlled by the motor 25a. By the motor 25a and/or the brake 26a, the expansion and contraction of the column unit 21 (the vertical movement of the holding unit 20) is stopped (braked).

The carriage unit 22 moves the column unit 21 relative to the ceiling 83 in the horizontal direction (X-direction). Specifically, the ceiling 83 is provided with a fixed rail 28a attached to the ceiling 83. The fixed rail 28a is provided on the ceiling 83 so as to extend in the Y-direction. The fixed rail 28a is also provided with movable rails 28b that are movable relative to the fixed rail 28a. The movable rail 28b is provided so as to extend in a direction (X-direction) perpendicular to the direction (Y-direction) in which the fixed rail 28a extends. The carriage unit 22 is provided with rollers 29. The carriage unit 22 is movably attached to the movable rails 28b via the rollers 29. When the movable rails 28b move along the fixed rail 28a in a state in which the carriage unit 22 is stationary with respect to the movable rail 28b, the column unit 21, the holding unit 20, and the X-ray generation unit 1 move in the Y-direction. In addition, when the carriage unit 22 moves along the movable rails 28b in a state in which the movable rails 28b are stationary with respect to the fixed rail 28a, the column unit 21, the holding unit 20, and the X-ray generation unit 1 move in the X-direction.

A motor 25b for moving, decelerating, and stopping the carriage unit 22 with respect to the movable rails 28b is provided inside the carriage unit 22. A brake 26b for stopping or braking the carriage unit 22 with respect to the movable rails 28b is provided inside the carriage unit 22. The movable rail 28b is also provided with a motor 25c for moving, decelerating, and stopping the movable rail 28b relative to the fixed rail 28a. The movable rail 28b is also provided with a brake 26c for stopping or braking the movable rail 28b relative to the fixed rail 28a.

The X-ray imaging apparatus 100 is provided with a cable 27 for supplying currents to the X-ray generation unit 1. The cable 27 is provided between the carriage unit 22 and the X-ray generation unit 1.

In this embodiment, the imaging unit 4 is arranged at a predetermined position and in a predetermined orientation with respect to the X-ray source 10 in the moving mechanism 2. Specifically, the imaging unit 4 is provided on the carriage unit 22 so as to be movable horizontally (in the X-direction and the Y-direction) integrally with the carriage unit 22. A plurality of imaging units 4 is provided on the carriage unit 22. The imaging units 4 are provided on the Y1-direction side and the Y2-direction side of the carriage unit 22, respectively. The two imaging units 4 are arranged in an angle fixed manner, respectively. In the example shown in FIG. 2, the imaging unit 4 is arranged in a direction along the irradiation direction of the X-rays (Z2-direction). With this, a region that becomes a blind spot due to the X-ray generation unit 1, the column unit 21, or the like, in one imaging unit 4 can be imaged by the other imaging unit 4.

(Operation Unit)

As shown in FIG. 3, the operation unit 7 includes a first button 71, a second button 72, and a third button 73. The first button 71, the second button 72, and the third button 73 are provided to the holding portion 74. The first button 71 is configured to be able to receive an input for preparing the X-ray irradiation. The second button 72 is configured to be able to receive an input for the X-ray irradiation. The third button 73 is configured to be able to receive an operation input for releasing the X-ray irradiation prohibited state. The first button 71 and the second button 72 are a so-called two-stage push-button switch.

When the first button 71 is pressed by an examiner 90, the X-ray imaging apparatus 100 starts a preparation operation for X-ray irradiation. Specifically, when the first button 71 is depressed to a position of the surface of the second button 72, the anode (or cathode) in the X-ray source 10 begins to rotate. After the rotational speed of the anode (or cathode) reaches a predetermined speed after the first button 71 is depressed, when the second button 72 is depressed together with the first button 71, X-rays are emitted from the X-ray source 10. That is, when the second button 72 is pressed for a predetermined period of time before the rotational speed of the anode (or cathode) reaches the predetermined speed after the first button 71 is pressed, the X-rays will not be emitted.

As will be described later, the control unit 5 is configured to perform control not to accept an operation input for X-ray irradiation to the operation unit 7 during the issuance of the caution information 40 by the notification unit 8. That is, when the caution information 40 is being issue, X-rays are prohibited from being emitted. Therefore, an examiner 90 can release the X-ray irradiation prohibited state by pressing the third button 73. After releasing the X-ray irradiation prohibited state, the examiner 90 can make the X-ray irradiation available by pressing the second button 72.

(Notification Processing)

Next, with reference to FIG. 4 to FIG. 9, the configuration in which the control unit 5 issues caution information 40 will be described.

When performing the X-ray imaging of a subject 91, the examiner 90 operates the operation unit 7 while checking the inside of the examination room 80 through the window 82. The area of the window 82 is often small. For example, in the example shown in FIG. 4, the examiner 90 can check the subject 91, the X-ray generation unit 1, a part of the moving mechanism 2, and the top board 9 through the window 82, so that not all of the inside of the examination room 80 can be checked. That is, the range within the examination room 80 that can be seen from the examiner 90 in the operation room 81 through the window 82 is limited.

Therefore, if a person 92 other than the subject 91 (see FIG. 5) is present in a position where the examiner 90 cannot see through the window 82, the examiner 90 may overlook the person 92. When carrying out the X-ray imaging of the subject 91, the examiner 90 needs to check that no person 92 other than the subject 91 is present in the examination room 80 so that the person 92 other than the subject 91 will not be exposed unnecessarily.

Therefore, in this embodiment, the control unit 5 is configured to perform control to make the notification unit 8 issue caution information 40 indicating that a person 92 other than the subject 91 is present in the examination room 80 when it is detected that a person 92 other than the subject 91 is present in the examination room 80 based on the imaging result obtained by the imaging unit 4.

Specifically, as shown in FIG. 5, the control unit 5 is configured to generate an image 50 of the inside of the examination room 80 based on the imaging result obtained by the imaging unit 4. The control unit 5 is configured to detect a person who is present in the examination room 80 based on the generated image 50 of the inside of the examination room 80.

In this embodiment, the control unit 5 is configured to distinguish between a person who is present in the examination room 80 and things other than a person by analyzing the image 50 of the inside of the examination room 80. In particular, the control unit 5 is configured to analyze the image 50 of the inside of the examination room 80 using a discriminator 41 that has been learned by machine learning. The control unit 5 is configured to detect a person who is present in the examination room 80 based on the analysis result using the discriminator 41.

Figure 6:
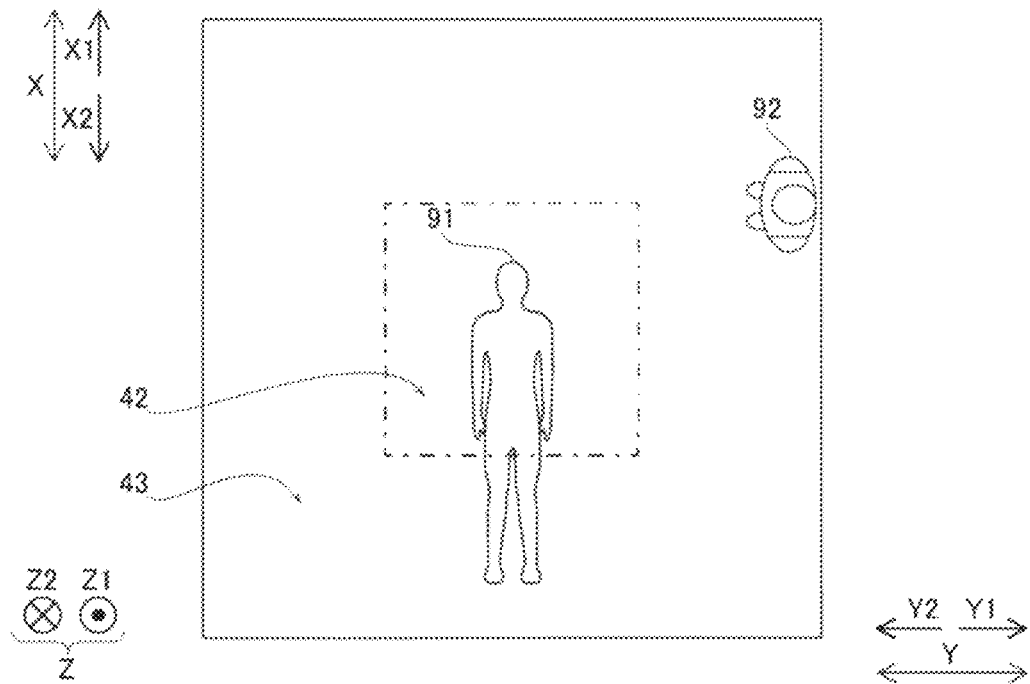
FIG. 6 is a schematic diagram showing a case in which a person other than a subject is present in a second region.

Further, in this embodiment, the control unit 5 is configured to determine whether or not to perform the notification by the notification unit 8, depending on the region where a person 92 other than the subject 91 is present in the examination room 80. More specifically, in this embodiment, as shown in FIG. 6, the control unit 5 sets, in the image 50 of the inside of the examination room 80, a first region 42 including the region where the subject 91 is present in the examination room 80 and a second region 43 outwardly adjacent to the first region 42 in the examination room 80. The first region 42 is a region outwardly adjacent to the subject 91 and is of a size that is not unnecessarily exposed to a person assisting the subject 91. In the case shown in FIG. 6, the region outwardly adjacent to the subject 91 and having a size allowing one person to enter is set as the first region 42. The second region 43 is a region of the entire examination room 80 positioned outside the first region 42. In the example shown in FIG. 6, the illustration of the top board 9 is omitted for the sake of convenience.

The control unit 5 is configured to perform control to make the notification unit 8 issue a notification when it is detected that a person is present at least in the second region 43 out of the first region 42 and the second region 43. That is, the control unit 5 is configured to make the notification unit 8 issue a notification when a person 92 other than the subject 91 is present outside the first region 42.

Note that when X-ray imaging of the subject 91 is performed, auxiliary such as an assistant of the subject 91 may be required in some cases. When assisting the subject 91, the X-ray irradiation needs to be performed in a state in which a person assisting the subject 91 (a person 92 other than the subject 91) is present in the examination room 80. Therefore, in this embodiment, when a person 92 other than the subject 91 is present in the first region 42, the control unit 5 regards the person 92 other than the subject 91 as an assistant, and allows the X-ray irradiation without issuing the notification by the notification unit 8. In addition, when the person 92 other than the subject 91 is too close to the subject 91, the person 92 other than the subject 91 is regarded as having a possibility of unnecessary exposure, and the notification by the notification unit 8 is performed. That is, the control unit 5 is configured to perform control to issue the notification by the notification unit 8 when a predetermined condition is satisfied when a person 92 other than the subject 91 is present in the first region 42.

Figure 7:
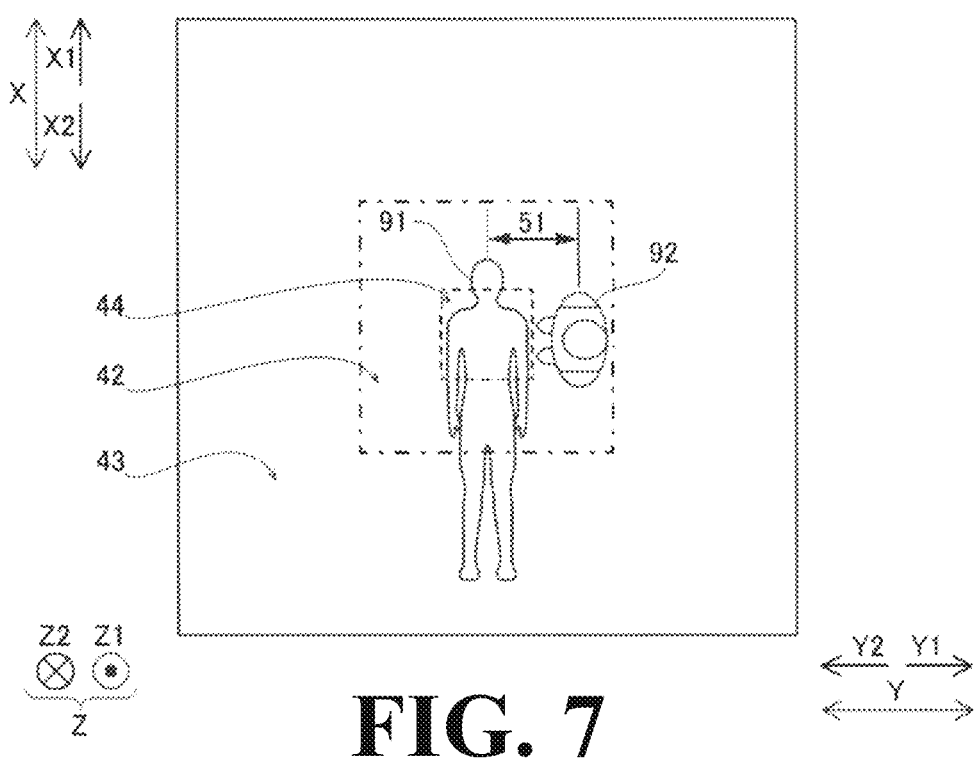
FIG. 7 is a schematic diagram showing a case in which a person other than a subject is present in a first region.

Specifically, as shown in FIG. 7, as the predetermined condition, the control unit 5 switches whether or not to issue the notification based on the distance 51 between the subject 91 and a person 92 other than the subject 91. More specifically, the control unit 5 is configured to perform control to issue the notification by the notification unit 8 when the distance 51 between the person 92 other than the subject 91 in the first region 42 and the subject 91 is equal to or smaller than a predetermined distance. That is, when the person 92 other than the subject 91 approached the subject 91 more than required, the control unit 5 make the notification unit 8 issue the caution information 40. In the example shown in FIG. 7, the illustration of the top board 9 is omitted for the sake of convenience.

When a person 92 other than the subject 91 supports the subject 91, the person 92 other than the subject 91 supports the subject 91 by hand or the like. Therefore, when the person 92 other than subject 91 supports the subject 91 by a hand or the like, the distance 51 from the subject 91 may become equal to or smaller than a predetermined distance. In view of this, in this embodiment, it is configured to perform control to issue a notification by the notification unit 8 based on the area of the image of the person 92 other than the subject 91 in the generated image 50 of the inside of the examination room 80.

Figure 8:
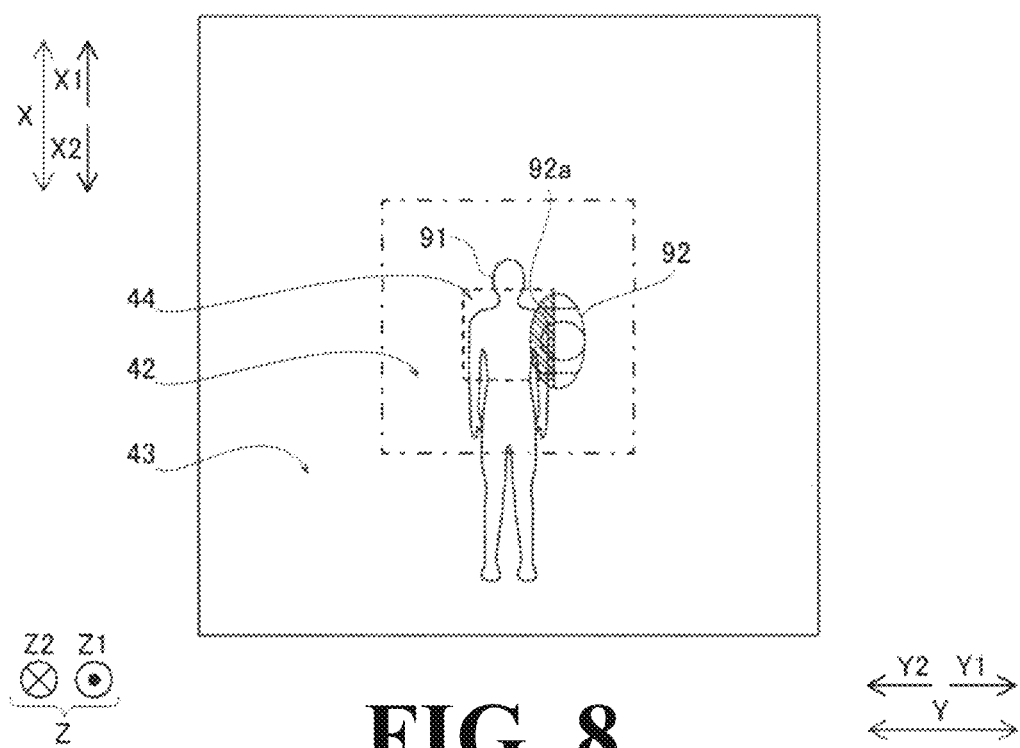
FIG. 8 is a schematic diagram showing a case in which a person other than a subject is present in an imaging region.

Specifically, as shown in FIG. 8, the control unit 5 sets an imaging region 44 where the X-rays in the first region 42 are irradiated in the generated image 50 of the inside of the examination room 80. As a predetermined condition, the control unit 5 is configured to perform control to make the notification unit 8 issue the notification when the area of the image of the person 92 other than the subject 91 present in the imaging region 44 is equal to or larger than a predetermined size. In the example shown in FIG. 8, among the image of the person 92 other than the subject 91, the image 92a in the imaging region 44 is shown by hatching. The control unit 5 is configured to determine whether the predetermined condition is met based on the size of the image 92a in the imaging region 44. In the example shown in FIG. 8, the illustration of the top board 9 is omitted for the sake of convenience.

Further, in this embodiment, the control unit 5 is configured to determine whether or not a person 92 other than the subject 91 is present in the examination room 80 when an input for X-ray irradiation preparation to the operation unit 7 is accepted. That is, the control unit 5 determines whether or not a person 92 other than the subject 91 is present in the examination room 80, triggered by the operation of the examiner 90 to perform the X-ray irradiation preparation. That is, when the first button 71 is pressed, the control unit 5 determines whether or not a person 92 other than the subject 91 is present in the examination room 80.

Figure 9:
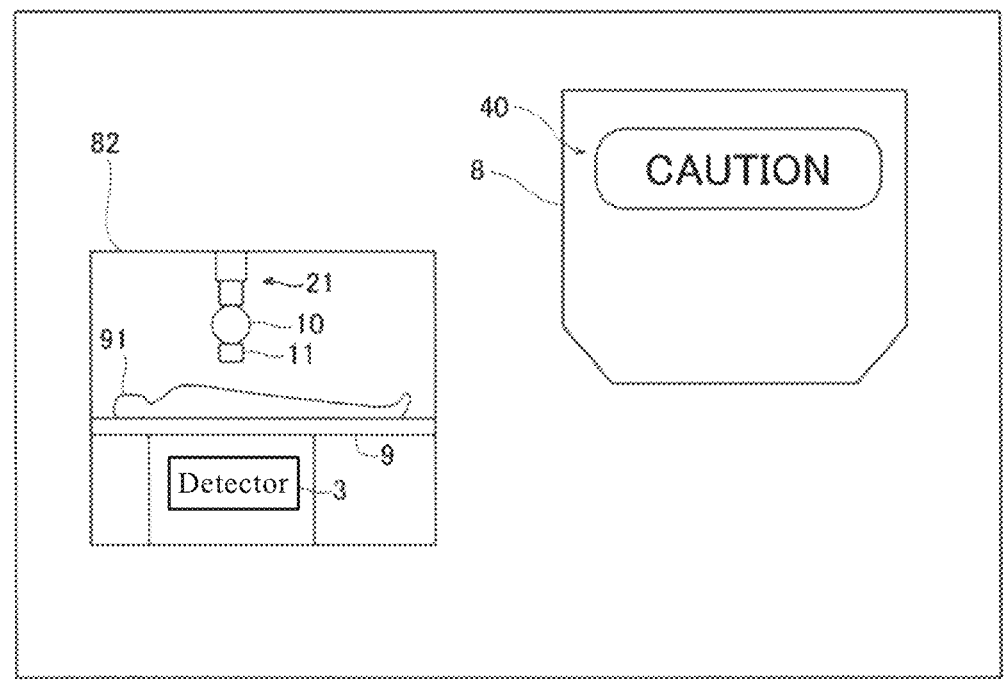
FIG. 9 is a schematic diagram for explaining an issuance of caution information in one embodiment.

The notification unit 8 is configured to issue the caution information 40 by warning light, warning sound, display of a warning message and/or display of the image 50 of the inside of the examination room 80. As shown in FIG. 9, in this embodiment, the notification unit 8 is configured to be able to display a message. For example, the notification unit 8 includes a liquid crystal monitor. The notification unit 8 is configured to provide the caution information 40 by displaying a warning message. In the embodiment shown in FIG. 9, the notification unit 8 is configured to display "CAUTION" as a warning message. It should be noted that not only the caution information 40 but also other information such as an X-ray imaging condition are displayed on the notification unit 8.

(Caution Information Notification Processing)

Figure 10:
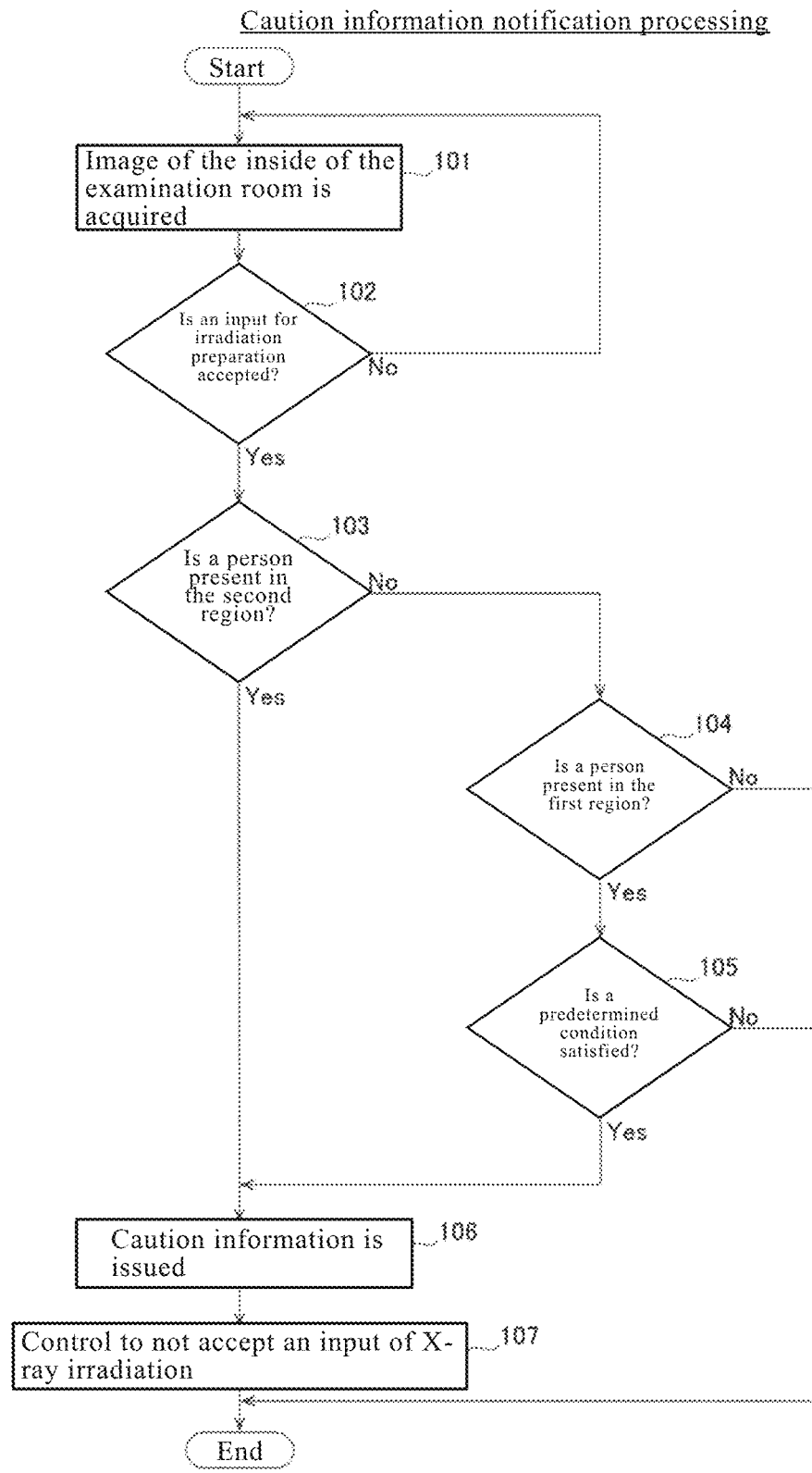
FIG. 10 is a flowchart for explaining a process of issuing caution information by a control unit according to an embodiment.

Next, with reference to FIG. 10, the notification processing of the caution information 40 by the control unit 5 will be described.

In Step 101, the control unit 5 acquires the image 50 of the inside of the examination room 80 captured by the imaging unit 4. Next, in Step 102, the control unit 5 determines whether or not an input for X-ray irradiation preparation to the operation unit 7 has been received. When the input for X-ray irradiation preparation to the operation unit 7 is received, the process proceeds to Step 103. When the input for X-ray irradiation preparation to the operation unit 7 has not been inputted, the process proceeds to Step101.

In Step 103, the control unit 5 determines whether a person is present in the second region 43 in the image 50 of the inside of the examination room 80. If no person is present in the second region 43, the process proceeds to Step104. If a person is present in the second region 43, the process proceeds to Step106.

In Step 104, the control unit 5 determines whether a person is present in the first region 42. If no person is present in the first region 42, the process ends. If a person is present in the first region 42, the process proceeds to Step105.

In Step 105, the control unit 5 determines whether or not a predetermined condition is satisfied. Specifically, the control unit 5 determines whether or not the distance 51 between the subject 91 and the person 92 other than the subject 91 and/or the area of the image 92a in the imaging region 44 is equal to or smaller than a predetermined size. If the predetermined condition is satisfied, the process proceeds to Step106. If the predetermined condition is not satisfied, the process ends.

In Step 106, the control unit 5 makes the notification unit 8 issue the caution information 40. Thereafter, the process proceeds to Step107.

In Step 107, the control unit 5 prohibits the acceptance of an operation input for X-ray irradiation. The control unit 5 may control hardware (second button 72) so as not to press the second button 72, for example, as a control for prohibiting the acceptance of the operation input for X-ray irradiation. Further, the control unit 5 may control software so that the software does not accept an input signal when the second button 72 is pressed, as the control for prohibiting the acceptance of the operation input for X-ray irradiation. Thereafter, the process ends.

(X-Ray Irradiation Prohibited State Release)

Figure 11:
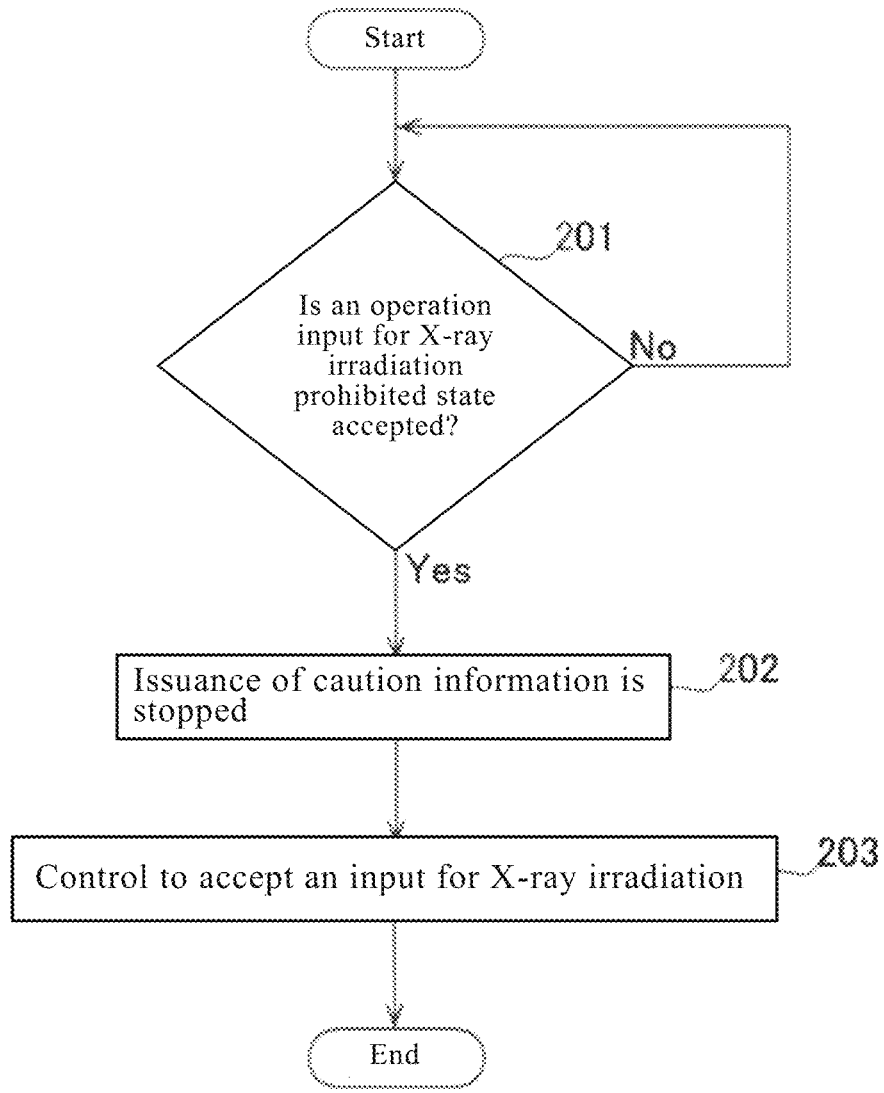
FIG. 11 is a flowchart for explaining a process in which a control unit releases an X-ray irradiation prohibited state according to an embodiment.

Next, with reference to FIG. 11, the process of releasing the X-ray irradiation prohibited state by the control unit 5 will be described.

In Step 201, the control unit 5 determines whether or not an operation input to release the X-ray irradiation prohibited state is accepted. Specifically, the control unit 5 determines whether or not the third button 73 is pressed. When the operation input to release the X-ray irradiation prohibited state is accepted, the process proceeds to Step 202. If the operation input to release the X-ray irradiation prohibited state has not been accepted, the process repeats Step 201.

In Step 202, the control unit 5 stops the notification of the caution information 40 by the notification unit 8. That is, when the person 92 other than the subject 91 is present in the second region 43, or when the person 92 other than the subject 91 is present in the first region 42 and a predetermined condition is satisfied, the control unit 5 issues the notification of the caution information 40 by the notification unit 8 from the time when the first button 71 is pressed until the third button 73 is pressed.

Next, in Step 203, the control unit 5 performs control to accept an operation input for X-ray irradiation. If the hardware is controlled so that the second button 72 cannot be pressed, the control unit 5 controls the hardware so that the second button 72 can be pressed. When the software is controlled so as not to accept the input signal when the second button 72 is pressed, the control unit 5 controls the software so as to accept the input signal when the second button 72 is pressed. Thereafter, the process ends. Either the processing of Step 202 or the processing of Step 203 may be performed first.

Effects of Embodiment

In this embodiment, the following effects can be obtained.

In this embodiment, as described above, the X-ray imaging apparatus 100 includes the X-ray source 10 arranged in the examination room 80, the detector 3 arranged in the examination room 80 for detecting X-rays emitted from the X-ray source 10, the imaging unit 4 for imaging a person present in the examination room 80, the operation unit 7 arranged outside the examination room 80 for receiving an operation input, the notification unit 8, and the control unit 5 for generating an image 50 of the inside of the examination room 80 based on the imaging result captured by the imaging unit 4 and for generating an image 50 in the examination room 80 based on control unit 5 photographed by imaging unit 4, and performing control to make the notification unit 8 issue the caution information 40 indicating that a person 92 other than the subject 91 is present in the examination room 80 when it is detected that a person 92 other than the subject 91 is present in the examination room 80 based on the generated image 50 of the inside of the examination room 80. With this, it is possible to alert the examiner 90 who performs the X-ray irradiation operation outside the examination room 80 that a person 92 other than the subject 91 is present in the examination room 80 without directly checking the inside of the examination room 80. As a result, it is possible to suppress the burden on examiner 90 from increasing, and it is also possible to notify that the person 92 other than the subject 91 is present in the examination room 80 even when the person 92 other than the subject 91 is present in a position where it is difficult to confirm through the window 82. In addition, for example, as compared with a configuration in which a person present in the examination room 80 is detected by a rangefinder such as an infra-red sensor or thermography, the positional relation of the person in the examination room 80 can be detected in detail. As a result, it is possible to improve the detecting accuracy of the person present in the examination room 80.

Further, in this embodiment, as described above, the control unit 5 is configured to perform the control to make the notification unit 8 issue the notification when it is detected that a person is present at least in the second region 43 out of the first region 42 including the region where the subject 91 is present in the examination room 80 and the second region 43 outwardly adjacent to the first region 42 in the examination room 80. Here, since the first region 42 is a region in which a person for assisting the subject 91 is present, when a window 82 for checking the inside of the examination room 80 is provided, at least the first region 42 can be checked. On the other hand, the second region 43 around the first region 42 may become a blind spot from the window 82. Therefore, by configuring as described above, since the caution information 40 is issued when a person is present in the second region 43, even when a person is present in the blind spot of the window 82 for checking the inside of the examination room 80, the examiner 90 can recognize that a person 92 other than the subject 91 is present in the examination room 80. As a result, when a person 92 other than the subject 91 is present in the blind spot of the window 82, the examiner 90 can be prevented from irradiating X-rays without checking the inside of the examination room 80, and therefore, it is possible to suppress the person 92 other than the subject 91 from being exposed to X-rays.

Further, in this embodiment, as described above, the control unit 5 is configured to perform the control to make the notification unit 8 issue the notification when a predetermined condition is satisfied when a person 92 other than the subject 91 is present in the first region 42. Here, the person in the first region 42 may be a person who assists the subject 91 who allows the X-ray irradiation or may be a third person to whom X-ray imaging should not be performed. Therefore, by configuring as described above, for example, the caution information 40 can be issue only when a person is present at a position satisfying a predetermined condition in the first region 42. As a result, when the notification by the notification unit 8 is not required, for example, when the person assisting the subject 91 is present in an appropriate position, the X-rays can be emitted without issuing the notification by the notification unit 8, so that the workability of the examiner 90 can be improved.

In addition, in this embodiment, as described above, the control unit 5 is configured to perform control, as a predetermined condition, to make the notification unit 8 issue the notification when the distance 51 between the subject 91 and a person 92 other than the subject 91 in the first region 42 is equal to or smaller than a predetermined distance. As a result, since the caution information 40 is issued when the person assisting the subject 91 approaches the subject 91 too close, the examiner 90 can grasp the fact that the person assisting the subject 91 approaches the subject 91 too close by the caution information 40 even when the examiner 90 cannot grasp the fact through the window 82. As a result, since the examiner 90 can be prompted to move to an appropriate position for the person assisting the subject 91, unnecessary exposure of the person assisting the subject 91 can be suppressed.

In addition, in this embodiment, as described above, the control unit 5 is configured to perform, as a predetermined condition, control to make the notification unit 8 issue the notification when the area of the image of the person 92 other than the subject 91 in the imaging region 44 irradiated with X-rays in the first region 42 is equal to or larger than a predetermined size. Thus, for example, when the person 92 other than the subject 91 covers the subject 91 more than required, the caution information 40 can be issued. In addition, even when the person 92 other than the subject 91 assists while covering the subject 91, when the area covering the subject 91 such as a hand is small, X-rays can be emitted without issuing the notification by the notification unit 8. As a result, it is possible to suppress unnecessary exposure of the person 92 other than the subject 91, and it is also possible to improve the workability of the examiner 90.

Further, in this embodiment, as described above, the control unit 5 is configured to determine whether or not a person 92 other than the subject 91 is present in the examination room 80 when the input for X-ray irradiation preparation to the operation unit 7 is accepted. As a result, it is possible to suppress an increase in the process burden of the control unit 5, as compared with a configuration in which it is determined whether or not a person 92 other than the subject 91 is present in the examination room 80 at all times, regardless of the manipulation on the operation unit 7. Further, for example, when the notification unit 8 also serves as a display device for displaying other information, the caution information 40 is not issued unless an input for X-ray irradiation preparation is accepted, so that other information can be displayed. As a result, the convenience of the examiner 90 can be improved.

Further, in this embodiment, as described above, the control unit 5 is configured to analyze the image 50 of the inside of the examination room 80 using the discriminator 41 that has been learned by machine learning, and to detect a person in the examination room 80 based on the analysis result using the discriminator 41. Thus, by using machine learning, it is possible to discriminate between a subject 91 and the person 92 other than the subject 91 even if the image is difficult to be discriminated by algorithms for discriminating between the subject 91 and the person 92 other than the subject 91 based on preset rules. As a result, it is possible to further improve the detecting accuracy of the person in the examination room 80.

Further, in this embodiment, as described above, the moving mechanism 2 for movably holding the X-ray source 10 is further provided, the moving mechanism 2 is provided on the ceiling 83 of the examination room 80, and the imaging unit 4 is provided on the moving mechanism 2. As a result, the imaging unit 4 can be arranged at a higher position, and the field of view at the time of imaging can be increased. As a result, even when the person 92 other than the subject 91 is present in a corner or the like in the examination room 80, the image can be taken by the imaging unit 4, and therefore, it is possible to improve the system for determining whether or not the person 92 other than the subject 91 is present.

In this embodiment, as described above, the imaging unit 4 is composed of a stereo camera. Thus, for example, compared with a configuration in which the position of the person 92 other than the subject 91 in the examination room 80 is acquired using one monocular camera, the person can be discriminated three-dimensionally. As a result, the position where the person 92 other than the subject 91 is located can be acquired with higher accuracy.

Further, in this embodiment, as described above, the imaging unit 4 is arranged at a predetermined position and in a predetermined orientation with respect to the X-ray source 10 in the moving mechanism 2. Thus, for example, when a stereo camera is used as the imaging unit 4, the position of the imaging unit 4 with respect to the moving mechanism 2 does not change, and thus the position of the cameras included in a stereo camera with respect to the moving mechanism 2 does not change. Therefore, the positional relation between the imaging result obtained by one camera of a stereo camera and the imaging result obtained by the other camera does not change. Thus, if the control unit 5 acquires the parameters for aligning each imaging result of the stereo camera once, it can generate the image 50 of the inside of the examination room 80 without acquiring the parameters for aligning each imaging result each time it generates the image 50 of the inside of the examination room 80. As a result, the process of generating the images 50 of the inside of the examination room 80 by the control unit 5 can be simplified.

Further, in this embodiment, as described above, the control unit 5 is configured to perform control not to accept an operation input for X-ray irradiation to the operation unit 7 during the notification of the caution information 40 by the notification unit 8. As a result, the X-ray irradiation can be prohibited during the notification of the caution information 40, so that the X-ray irradiation can be prevented even when the operation unit 7 is operated by mistake when a person 92 other than the subject 91 is present in the examination room 80. As a result, it is possible to further suppress the exposure of the person 92 other than the subject 91.

Further, in this embodiment, as described above, the operation unit 7 is configured to be able to accept an operation input for releasing the X-ray irradiation prohibited state. As a result, this makes it possible for the examiner 90 to perform the release operation of the X-ray irradiation prohibition, so that X-ray irradiation can be performed after determining whether or not the examiner 90 may perform X-ray irradiation. As a result, it is possible to suppress the examiner 90 from erroneously emitting X-rays.

Further, in this embodiment, as described above, the notification unit 8 is configured to issue the caution information 40 by at least one of warning light, warning sound, the display of a warning message, and the display of the image 50 of the inside of the examination room 80. Thereby, the caution information 40 can be visually and/or audibly issued. As a result, the examiner 90 can more intuitively grasp the presence of a person 92 other than the subject 91 in the examination room 80.

[Modifications]

It should be noted that the embodiment disclosed herein is to be considered in all respects as illustrative and not restrictive. The scope of the present invention is indicated by claims rather than by the embodiment described above, and includes all modifications within the meanings and ranges equivalent to claims.

(First Modification)

Figure 12:
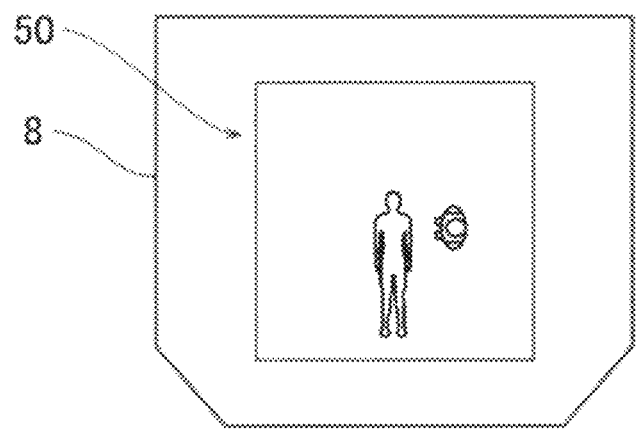
FIG. 12 is a schematic diagram for explaining an issuance of caution information in a first modification.

For example, in the above embodiment, an example is shown in which the notification unit 8 issues the caution information 40 by displaying a warning message, but the present invention is not limited to this. For example, as in the first modification shown in FIG. 12, the notification unit 8 may be configured to issue the caution information 40 by displaying the image 50 of the inside of the examination room 80. The notification unit 8 may also include an LED and be configured to issue the caution information 40 by flashing warning light. The notification unit 8 may include a speaker or the like, and may be configured to issue the caution information 40 by warning sound or the like. The notification unit 8 may also be configured to issue the caution information 40 by combining a display of a warning message, a display of an image 50 of the inside of the examination room 80, lighting (or flashing) of warning light, and warning sound.

(Second Modification)

Figure 13:
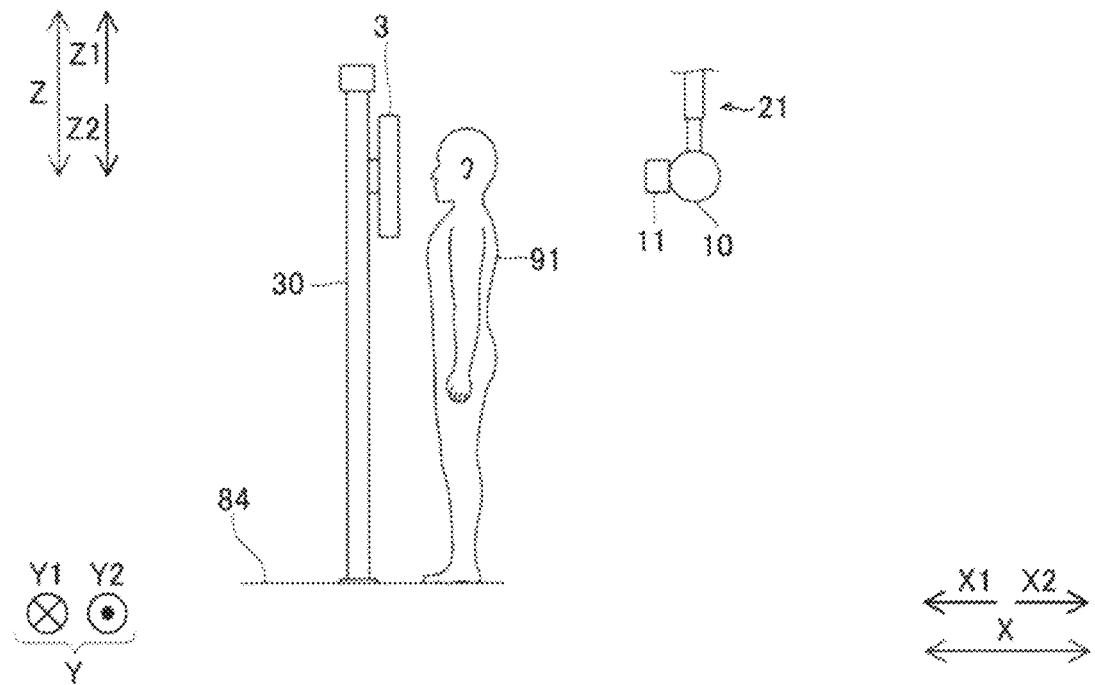
FIG. 13 is a schematic diagram for explaining imaging by an X-ray imaging apparatus according to a second modification.
Figure 14:
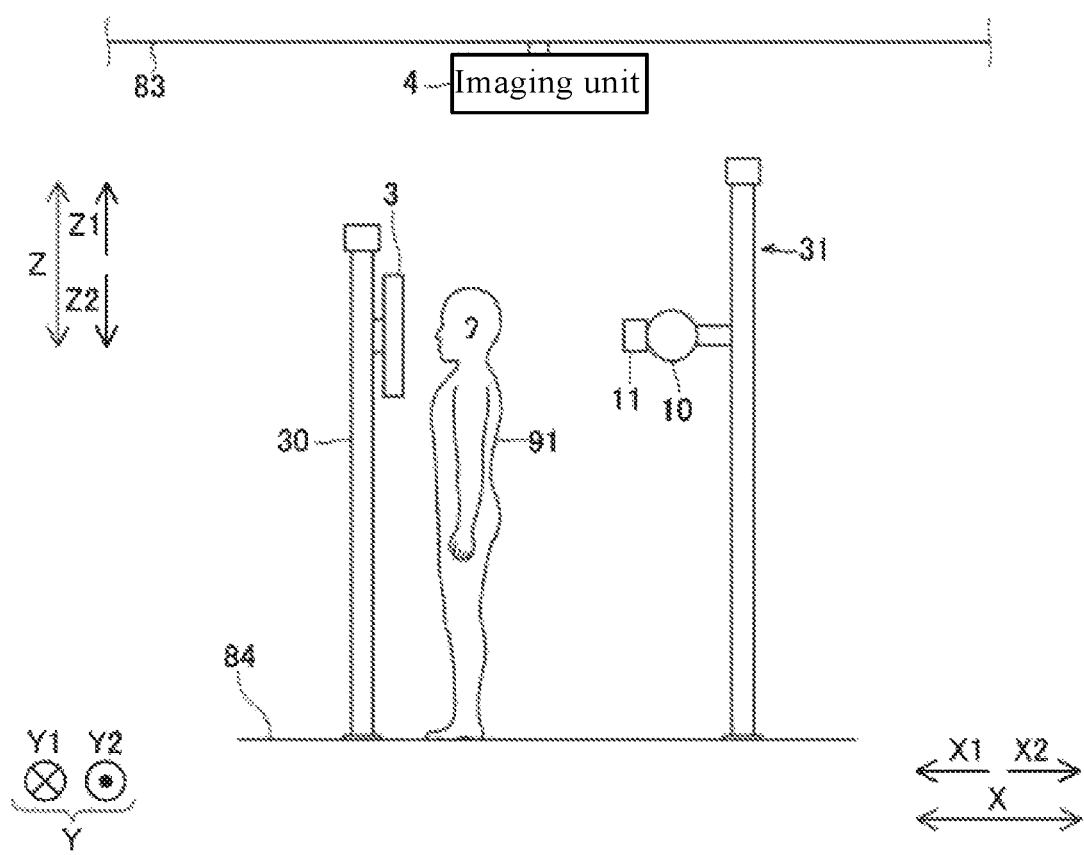
FIG. 14 is a schematic diagram for explaining a configuration of an X-ray imaging apparatus according to a third modification.

In the above embodiment, an example is shown in which the subject 91 is imaged while lying on the top board 9, but the present invention is not limited to this. For example, as in the second modification shown in FIG. 13, the camera may be configured to perform imaging in a standing position of the subject 91. When the subject 91 is imaged in an upright position, the position and orientation of the X-ray generation unit 1 may be adjusted so that X-rays are emitted in the X-direction. In addition, the detector holding unit 30 for holding the detector 3 may be provided on the examination room 80 floor 84, and the detector 3 may be held so that the detecting surface of the detector 3 faces the X-ray source 10 in the detector holding unit 30.

(Third Modification)

In the above embodiment, an example is shown in which the X-ray source 10 (X-ray generation unit 1) is held in the moving mechanism 2 provided on the ceiling 83 of the examination room 80, but the present invention is not limited thereto. For example, as in the third modification shown in FIG. 13, the X-ray source 10 may be configured to be held in the X-ray source holding unit 31 provided on the floor 84 of the examination room 80. The X-ray source holding unit 31 is configured to move the X-ray source 10 in the Z-direction. When the X-ray source 10 is provided on the X-ray source holding unit 31, the imaging unit 4 may be provided on the ceiling 83.

(Other Modifications)

In the above embodiment, an example is shown in which the two imaging units 4 are provided in the moving mechanism 2, but the present invention is not limited to this. For example, the moving mechanism 2 may be provided with one imaging unit 4. However, when the imaging unit 4 is one, a blind spot occurs due to the column unit 21 or the like, and therefore, it is preferable to provide a plurality of imaging units 4.

In the above embodiment, the imaging unit 4 is composed of a stereo camera, but the present invention is not limited to this. For example, the imaging unit 4 may be configured to function as a stereo camera by combining two monocular cameras.

In the above embodiment, an example is shown in which the X-ray imaging apparatus 100 includes the imaging unit 4, but the present invention is not limited thereto. For example, the X-ray imaging apparatus 100 may include an infra-red sensor, an ultrasonic rangefinder, thermography, etc. The X-ray imaging apparatus 100 may include any member so long as it can detect a person in the examination room 80.

In the above embodiment, an example is shown in which the operation unit 7 includes the first button 71, the second button 72, and the third button 73, but the present invention is not limited thereto. For example, the first button 71, the second button 72, and the third button 73 may not be provided on the same operation unit, but on an operation unit located at different positions. However, since the operation for X-ray irradiation preparation and the operation for X-ray irradiation are performed in a series of flows, the first button 71 and the second button 72 should be provided on the same operation unit. Further, since the operation of releasing the X-ray irradiation prohibited state is an operation performed prior to the X-ray irradiation operation in a condition in which the X-ray irradiation is prohibited, it is preferable that the third button 73 is also provided in the vicinity of the first button 71 and the second button 72.

In the above embodiment, an example is shown in which the imaging unit 4 is provided in the moving mechanism 2, but the present invention is not limited to this. For example, the imaging unit 4 may be provided on the ceiling 83 of the examination room 80. However, when the imaging unit 4 is provided on the ceiling 83 of the examination room 80, the relative position of the imaging unit 4 and the relative position of the X-ray source 10 change as the X-ray source 10 moves. Therefore, each time the X-ray generation unit 1 is moved by the moving mechanism 2, the image 50 of the inside of the examination room 80 must be calibrated. Therefore, the imaging unit 4 is preferably provided on the moving mechanism 2.

In the above embodiment, an example is shown in which the imaging unit 4 is arranged in the direction along the X-ray irradiating direction (Z2-direction), but the present invention is not limited thereto. The imaging unit 4 may be inclined with respect to the X-ray irradiating direction (Z2-direction).

Further, in the above embodiment, an example is shown in which the control unit 5 determines whether or not a person 92 other than the subject 91 is present in the examination room 80 when receiving an input for X-ray irradiation preparation, but the present invention is not limited thereto. For example, the control unit 5 may be configured to constantly determine whether or not a person 92 other than the subject 91 is present in the examination room 80. However, when the control unit 5 constantly determines whether or not a person 92 other than the subject 91 is present in the examination room 80, the process burden increases. Therefore, it is preferable that the control unit 5 is configured to determine whether or not a person 92 other than the subject 91 is present in the examination room 80 when the X-ray irradiation preparation is inputted.

In the above embodiment, an example is shown in which the control unit 5 analyzes the image 50 of the inside of the examination room 80 using the discriminator 41 that has been learned by machine learning to detect a person in the examination room 80, but the present invention is not limited to this. For example, the control unit 5 may be configured to detect a person in the examination room 80 by the so-called rule-based algorithms.

In the above embodiment, an example is shown in which when a person 92 other than the subject 91 is present in the first region 42, the control unit 52 issues the notification when a predetermined condition is satisfied, but the present invention is not limited to this. For example, the control unit 5 may be configured to make the notification unit 8 issue the notification unconditionally when a person 92 other than the subject 91 is present in the first region 42.

In the above embodiment, an example is shown in which the control unit 5 prohibits the X-ray irradiation during the notification of the caution information 40, but the present invention is not limited to this. For example, the control unit 5 may not prohibit X-ray irradiation during the notification of the caution information 40.

Further, in the above embodiment, an example is shown in which the notification of the caution information 40 by the notification unit 8 is stopped when the third button 73 is pressed, but the present invention is not limited to this. For example, the notification of the caution information 40 by the notification unit 8 may be stopped when the first button 71 or the second button 72 is pressed during the notification of the caution information 40 by the notification unit 8. In addition, a fourth button for stopping the issuance of the caution information 40 by the notification unit 8 may be provided, and when the fourth button is pressed, the issuance of the caution information 40 by notification unit 8 may be stopped.

[Aspects]

It will be appreciated by those skilled in the art that the above described exemplary embodiments are illustrative of the following aspects.

(Item 1)

An X-ray imaging apparatus comprising:
an X-ray source arranged in an examination room;
a detector arranged in the examination room to detect X-rays emitted from the X-ray source;
an imaging unit configured to image a person who is present in the examination room;
an operation unit arranged outside the examination room to accept an operation input;
a notification unit; and
a control unit configured to generate an image of an inside of the examination room based on an imaging result captured by the imaging unit and configured to perform control to make the notification unit issue caution information indicating that a person other than a subject is present in the examination room when the person other than the subject is present in the examination room is detected based on the generated image of the inside of the examination room.

(Item 2)

The X-ray imaging apparatus as recited in the aforementioned Item 1,
wherein the control unit is configured to perform control to make the notification unit issue the caution information when it is detected that a person is present, out of a first region including a region in the examination room where the subject is present and a second region outwardly adjacent to the first region in the examination room, at least in the second region.

(Item 3)

The X-ray imaging apparatus as recited in the aforementioned Item 2,
wherein the control unit is configured to perform control to make the notification unit issue the caution information when a predetermined condition is satisfied in cases where the person other than the subject is present in the first region.

(Item 4)

The X-ray imaging apparatus as recited in the aforementioned Item 3,
wherein the control unit is configured to perform control to make the notification unit issue the caution information when a distance from the person other than the subject who is present in the first region to the subject is equal to or smaller than a predetermined distance, as the predetermined condition.

(Item 5)

The X-ray imaging apparatus as recited in the aforementioned Item 4,
wherein the control unit is configured to perform control to make the notification unit issue the caution information when an area of an image of the person other than the subject in an imaging region in the first region to which X-rays are irradiated is equal to or larger than a predetermined size, as the predetermined condition, (Item 6)

The X-ray imaging apparatus as recited in the aforementioned Item 1,
wherein the control unit is configured to determine whether or not the person other than the subject is present in the examination room when an input for X-ray irradiation preparation to the operation unit is accepted.

(Item 7)

The X-ray imaging apparatus as recited in the aforementioned Item 1,
wherein the control unit is configured to analyze the image of the inside of the examination room using a discriminator that has been learned by machine learning to detect a person who is present in the examination room based on an analysis result using the discriminator.

(Item 8)

The X-ray imaging apparatus as recited in the aforementioned Item 7, further comprising:
a moving mechanism configured to movably hold the X-ray source,
wherein the moving mechanism is provided on a ceiling of the examination room, and
wherein the imaging unit is provided on the moving mechanism.

(Item 9)

The X-ray imaging apparatus as recited in the aforementioned Item 8,
wherein the imaging unit is composed of a stereo camera.

(Item 10)

The X-ray imaging apparatus as recited in the aforementioned Item 8,
wherein the imaging unit is arranged in the moving mechanism at a predetermined position and in a predetermined orientation with respect to the X-ray source.

(Item 11)

The X-ray imaging apparatus as recited in the aforementioned Item 1,
wherein the control unit is configured to perform control not to accept an operation input for X-ray irradiation to the operation unit during the caution information is being issued by the notification unit.

(Item 12)

The X-ray imaging apparatus as recited in the aforementioned Item 11,
wherein the operation unit is configured to be able to accept an operation input for releasing an X-ray irradiation prohibited state.

(Item 13)

The X-ray imaging apparatus as recited in the aforementioned Item 1,
wherein the notification unit is configured to issue the caution information by at least one of warning light, warning sound, a display of a warning message, and a display of an image of the inside of the examination room.

The invention claimed is:

1. An X-ray imaging apparatus comprising:
an X-ray source arranged in an examination room;
a detector arranged in the examination room to detect X-rays emitted from the X-ray source;
an imaging unit configured to image a person who is present in the examination room;
an operation unit arranged outside the examination room to accept an operation input;
a notification unit; and
a control unit configured to generate an image of an inside of the examination room based on an imaging result captured by the imaging unit and configured to perform control to make the notification unit issue caution information indicating that a person other than a subject is present in the examination room when the person other than the subject is present in the examination room is detected based on the generated image of the inside of the examination room.

2. The X-ray imaging apparatus as recited in claim 1,
wherein the control unit is configured to perform control to make the notification unit issue the caution information when it is detected that a person is present, out of a first region including a region in the examination room where the subject is present and a second region outwardly adjacent to the first region in the examination room, at least in the second region.

3. The X-ray imaging apparatus as recited in claim 2,
wherein the control unit is configured to perform control to make the notification unit issue the caution information when a predetermined condition is satisfied in cases where the person other than the subject is present in the first region.

4. The X-ray imaging apparatus as recited in claim 3,
wherein the control unit is configured to perform control to make the notification unit issue the caution information when a distance from the person other than the subject who is present in the first region to the subject is equal to or smaller than a predetermined distance, as the predetermined condition.

5. The X-ray imaging apparatus as recited in claim 4,
wherein the control unit is configured to perform control to make the notification unit issue the caution information when an area of an image of the person other than the subject in an imaging region in the first region to which X-rays are irradiated is equal to or larger than a predetermined size, as the predetermined condition.

6. The X-ray imaging apparatus as recited in claim 1,
wherein the control unit is configured to determine whether or not the person other than the subject is present in the examination room when an input for X-ray irradiation preparation to the operation unit is accepted.

7. The X-ray imaging apparatus as recited in claim 1,
wherein the control unit is configured to analyze the image of the inside of the examination room using a discriminator that has been learned by machine learning to detect a person who is present in the examination room based on an analysis result using the discriminator.

8. The X-ray imaging apparatus as recited in claim 7, further comprising:
a moving mechanism configured to movably hold the X-ray source,
wherein the moving mechanism is provided on a ceiling of the examination room, and
wherein the imaging unit is provided on the moving mechanism.

9. The X-ray imaging apparatus as recited in claim 8,
wherein the imaging unit is composed of a stereo camera.

10. The X-ray imaging apparatus as recited in claim 8,
wherein the imaging unit is arranged in the moving mechanism at a predetermined position and in a predetermined orientation with respect to the X-ray source.

11. The X-ray imaging apparatus as recited in claim 1,
wherein the control unit is configured to perform control not to accept an operation input for X-ray irradiation to the operation unit during the caution information is being issued by the notification unit.

12. The X-ray imaging apparatus as recited in claim 11,
wherein the operation unit is configured to be able to accept an operation input for releasing an X-ray irradiation prohibited state.

13. The X-ray imaging apparatus as recited in claim 1,
wherein the notification unit is configured to issue the caution information by at least one of warning light, warning sound, a display of a warning message, and a display of an image of the inside of the examination room.

* * * * *